United States Patent
Rocchi et al.

(10) Patent No.: US 10,538,891 B2
(45) Date of Patent: Jan. 21, 2020

(54) PENETROMETER

(71) Applicant: ALMA MATER STUDIORUM—UNIVERSITA' DI BOLOGNA, Bologna (IT)

(72) Inventors: Irene Rocchi, Bologna (IT); Laura Tonni, Casalecchio di Reno (IT); Guido Gottardi, Bologna (IT)

(73) Assignee: ALMA MATER STUDIORUM—UNIVERSITA' DI BOLOGNA, Bologna (IT)

( * ) Notice: Subject to any disclaimer, the term of this patent is extended or adjusted under 35 U.S.C. 154(b) by 0 days.

(21) Appl. No.: 16/305,193

(22) PCT Filed: May 26, 2017

(86) PCT No.: PCT/IB2017/053104
§ 371 (c)(1),
(2) Date: Nov. 28, 2018

(87) PCT Pub. No.: WO2017/212366
PCT Pub. Date: Dec. 14, 2017

(65) Prior Publication Data
US 2019/0338483 A1    Nov. 7, 2019

(30) Foreign Application Priority Data
Jun. 8, 2016 (IT) .................. 102016000058758

(51) Int. Cl.
*G01N 33/24* (2006.01)
*E02D 1/02* (2006.01)
(52) U.S. Cl.
CPC .............. *E02D 1/025* (2013.01); *G01N 33/24* (2013.01)

(58) Field of Classification Search
CPC ................................ G01N 33/24; E02D 1/025
USPC ............................................................. 73/84
See application file for complete search history.

(56) References Cited

U.S. PATENT DOCUMENTS

| | | | | |
|---|---|---|---|---|
| 5,165,274 A * | 11/1992 | Thiercelin | ............. | E21B 49/006 73/152.59 |
| 6,164,126 A * | 12/2000 | Ciglenec | ................. | E21B 49/10 73/152.01 |
| 2007/0158062 A1* | 7/2007 | Heller | ..................... | E21B 34/12 166/69 |
| 2008/0083266 A1* | 4/2008 | Gupta | .................... | G01N 15/08 73/38 |
| 2010/0257920 A1* | 10/2010 | Lee | ......................... | E02D 1/022 73/84 |

FOREIGN PATENT DOCUMENTS

| CN | 101858073 A | 10/2010 |
|---|---|---|
| CN | 204112301 U | 1/2015 |
| EP | 2 385 175 A2 | 11/2011 |

OTHER PUBLICATIONS

Patent Cooperation Treaty (PCT), International Search Report and Written Opinion issued in PCT Application No. PCT/IB2017/053104 (International Filing Date May 26, 2017), dated Jul. 21, 2017 (10 pgs).

\* cited by examiner

*Primary Examiner* — Jamel E Williams
(74) *Attorney, Agent, or Firm* — Kraguljac Law Group, LLC

(57) ABSTRACT

Provided are a testing instrument and method for checking the degree of saturation of a pressure sensor unit of a piezocone.

15 Claims, 2 Drawing Sheets

PENETROMETER

TECHNICAL FIELD

This invention has for its object a testing instrument for checking the degree of saturation of a pressure sensor unit of a piezocone.

More specifically, the instrument is a testing instrument for checking the degree of saturation of a pressure sensor unit which is configured to measure the interstitial pressure of the soil and which forms part of a piezocone. Generally speaking, the term "piezocone" is used to mean a static penetrometer with an electric tip which measures at least the interstitial pressure of the soil (as well as the penetration resistance and lateral friction applied by the soil on the piezocone).

This invention also has for its objects a method for performing such a check and an apparatus comprising a piezocone associated with the instrument.

BACKGROUND ART

More specifically, the piezocone is adapted to perform static penetrometric tests.

Static penetrometric testing has, in recent years, become the most widespread method of obtaining in situ information on the stratigraphic and characteristic properties of soil deposits. In particular, the static penetrometric test with measurement of interstitial pressures (hereinafter called piezocone test), although introduced relatively recently, has already become a standard test in the range of possible in situ geotechnical tests, thanks to its relative simplicity, low cost and wealth of available experience. The possibility of measuring interstitial pressures in the soil during the test significantly improves the quality of the stratigraphic profile obtained from a static penetrometric test because it allows identifying even thin soil lenses and is more accurate in estimating the mechanical parameters.

The piezocone acts as a probe which measures the resistance of the soil when the piezocone is pushed into it.

One type of piezocone which may be used in stratigraphic analysis extends along an axis of extension.

The piezocone includes a pressure sensor unit to measure the interstitial pressure of the soil. The interstitial pressure of the soil, also called "interstitial overpressure" develops when the piezocone is pushed into the soil. The sensor unit comprises a pressure transducer inside the piezocone.

The pressure transducer may operate, for example, by deflection of a blade.

The sensor unit comprises a porous annular element designed to prevent agglomerates or particles of excessive size from finding their way into the sensor unit.

The lateral outside surface of the porous annular element defines a surface portion of the piezocone situated around the axis of extension of the piezocone itself.

To cause the interstitial pressure of the soil to be propagated as far as the pressure transducer, the sensor unit comprises a duct inside the piezocone, interposed between the porous annular element and the transducer so that the transducer can measure the pressure applied to the aforesaid surface portion. As mentioned above, this surface portion coincides with the lateral outside surface of the porous annular element. During use of the piezocone, the sensor unit contains a working liquid, which may be different from the interstitial liquid which is present in the soil and whose pressure, known as interstitial pressure or soil pore pressure, is to be measured. The working liquid is at least partly in equilibrium with the interstitial liquid so that variations in the pressure of the interstitial liquid produce corresponding variations in the pressure of the working liquid and hence corresponding variations measured by the sensor unit.

During measurement of the interstitial pressure, the working liquid may contain air bubbles. These air bubbles may form when the piezocone is assembled and or they may be the result of non-saturation of the porous annular element or of cavitation phenomena in the working liquid inside the porous annular element E which may occur when the tip of the piezocone penetrates soils that produce a negative overpressure.

The air bubbles cause a certain amount of deformability in the mass of liquid contained in the sensor unit, in the sense that part of the interstitial overpressure to be measured, generated in the soil and acting on the lateral outside surface of the porous annular element, is used to compress the air bubbles. In this case, the liquid in the sensor unit becomes "compressible", and in some cases to non-negligible levels.

At present, apparatuses are available which allow improving the saturation of the sensor unit by eliminating at least part of the air bubbles. Examples of such apparatuses are described in patent documents CN101858073 and CN204112301.

These apparatuses do not allow assessing the level or degree of saturation of the pressure sensor.

DISCLOSURE OF THE INVENTION

The aim of this description is to provide a testing instrument for checking the degree of saturation (or the current level or degree of saturation, that is to say, the level or degree when the measurement is performed) of a pressure sensor unit of a piezocone and a method for performing the check, allowing the check to be carried out in situ, that is, in the field.

Another aim of this description is to provide a testing instrument for checking the degree of saturation of a pressure sensor unit of a piezocone and a method for performing the check, allowing the check to be carried out rapidly and just before the piezocone is used.

Another aim of this description is to provide a testing instrument for checking the degree of saturation of a pressure sensor unit of a piezocone and a method for performing the check, allowing the check to be carried after the piezocone has been used to check whether the degree of saturation changed while the piezocone was being used.

Another aim of this description is to provide a testing instrument for checking the degree of saturation of a pressure sensor unit of a piezocone and which is compact and easy to transport together with the piezocone itself.

A further aim of this invention is to provide a measuring instrument for measuring the interstitial pressure which develops when a piezocone is pushed into the soil during stratigraphic analysis of soils and which comprises a testing instrument for checking the degree of saturation of a pressure sensor unit of the piezocone.

These aims are fully achieved by the testing instrument, method and apparatus forming the objects of this description and which can be characterized by the contents of one or more of the claims appended to this application and relating to the instrument, method and apparatus, respectively.

More specifically, this description relates to a testing instrument for checking the degree of saturation of a pressure sensor unit of a piezocone, comprising:

an annular structure which extends around a passage adapted to receive the piezocone by insertion into the passage;

a membrane which delimits the annular structure defining an annular surface facing the passage, to be operatively in contact with a porous annular element of the sensor unit of the piezocone;

a pressurizer operating on the membrane to transmit a pressure pulse of predetermined intensity to the membrane.

According to another aspect, this description relates to a testing method for checking the degree of saturation of a pressure sensor unit of a piezocone, comprising the following steps:

generating a pressure pulse of known intensity;

transmitting the pulse to the lateral outside surface of a porous annular element of the sensor unit;

acquiring a pressure value measured by a pressure transducer of the sensor unit in response to the pressure pulse transmitted;

comparing the acquired value with the known intensity of the generated pulse.

According to a further aspect, this description relates to an apparatus for measuring soil interstitial pressure which develops when a piezocone for soil stratigraphic analysis is pushed into the soil, the apparatus comprising:

a piezocone;

a testing instrument according to this description.

BRIEF DESCRIPTION OF THE DRAWINGS

The features of the instrument, method and apparatus according to this description will become more apparent from the following description of respective embodiments of the instrument, method and apparatus, provided purely as non-limiting examples, with reference to the accompanying drawings, in which.

DETAILED DESCRIPTION OF PREFERRED EMBODIMENTS OF THE INVENTION

Figure 2:
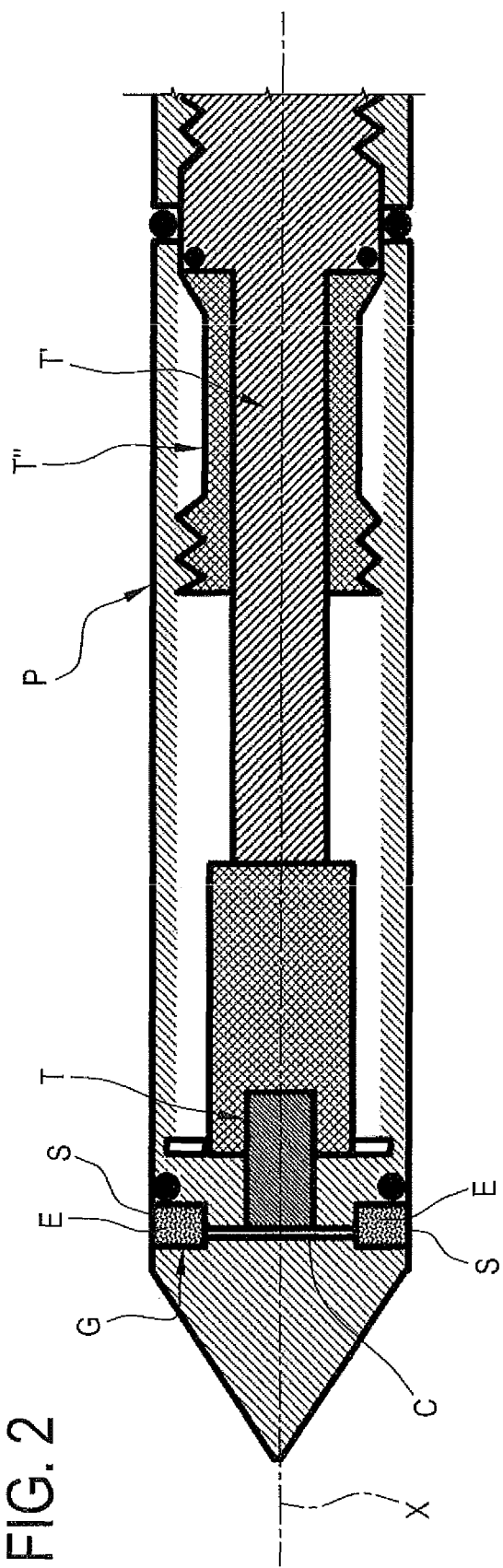
FIG. 2 is a lateral cross section of an example of a piezocone for stratigraphic analyses.
Figure 3:
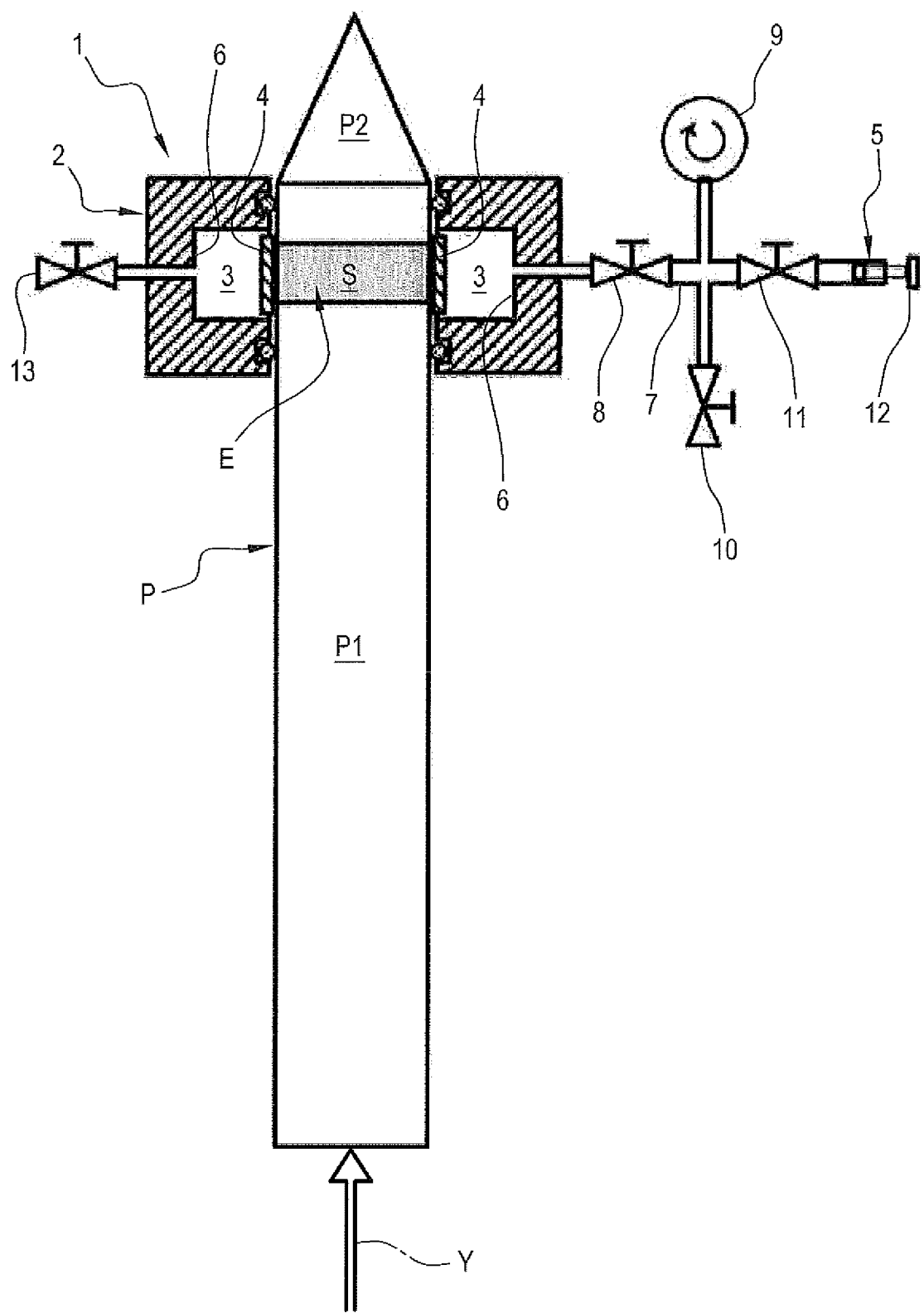
FIG. 3 shows the instrument according to a possible embodiment of this description in a situation where the instrument is fitted to the piezocone and where only the instrument is shown partly in cross section.

FIGS. 2 and 3 show a piezocone P which includes a pressure sensor unit configured to measure the interstitial pressure which develops when the piezocone P is pushed into the soil. The sensor unit is labelled G.

The interstitial pressure is the pressure applied by at least one interstitial liquid present in the pores of the soil and may also be called "interstitial overpressure".

Generally speaking, the piezocone P is a type of penetrometer used for stratigraphic analyses and which also allows interstitial soil pressures to be measured.

The piezocone P shown by way of example in the accompanying drawings comprises a cylindrical body P1 and a tapered head or tip P2. The piezocone P extends along an axis of extension X running through the cylindrical body P1 and the tapered head P2.

In FIG. 3, the piezocone P is shown from a plane parallel to the axis of extension X, indicated only in FIG. 2, whilst in FIG. 2, the piezocone P is shown in cross section through a plane containing the axis of extension X.

In the example piezocone P shown in FIGS. 2 and 3, the sensor unit G comprises a porous annular element E whose lateral outside surface S defines a surface portion of the piezocone P situated around its axis of extension X.

In the example piezocone P shown in the accompanying drawings, this surface portion, which coincides with the lateral outside surface S of the porous annular element E, is situated on the cylindrical body P1 and is therefore a cylindrical surface situated around the axis of extension X of the piezocone P.

As may be noticed in FIG. 2, the example of the sensor unit G shown in the accompanying drawings comprises a pressure transducer T inside the piezocone P, and a duct C interposed between the porous annular element E and the transducer T in such a way that the transducer T can measure the pressure applied on the surface portion of the piezocone P which coincides with the lateral outside surface S of the porous annular element E.

FIG. 2 shows two sectors of the porous annular element E. These sectors of the porous annular element E are situated on mutually opposite sides of the axis of extension X of the piezocone P and are visible in cross section in FIG. 2.

FIG. 2 accordingly also shows two sectors of the lateral outside surface S of the porous annular element E. These sectors of the lateral outside surface S of the porous annular element E are defined by the respective sectors of the porous annular element E, mentioned above and visible in cross section in FIG. 2. Thus, these sectors of the lateral outside surface S are also situated on mutually opposite sides of the axis of extension X and are shown in cross section, thus coinciding with respective lines.

To measure the penetration resistance applied by the soil to the piezocone P, the piezocone P preferably includes one or more strain transducers or load cells.

In a possible embodiment, the piezocone P includes a (first) strain transducer T' configured for (and disposed in such a was to be capable of) measuring the axial strains acting on the piezocone P along its axis of extension X and producing an axial force. These strains are correlated respectively with the penetration resistance which the soil applies on the tip of the piezocone P (axial force).

In a possible embodiment, the piezocone P (also) includes a (second) strain transducer T" configured for (and disposed in such a was to be capable of) measuring the tangential strains acting on its lateral outside surface, situated around its axis of extension X and producing a tangential or cutting force. These strains are correlated respectively with the lateral friction applied by the soil on the piezocone P (tangential force).

Thus, the piezocone P can also be configured to measure the strains acting on the piezocone P transversely and, preferably, at right angles to its axis of extension X and thus, the transverse force acting on the piezocone P.

Figure 1:
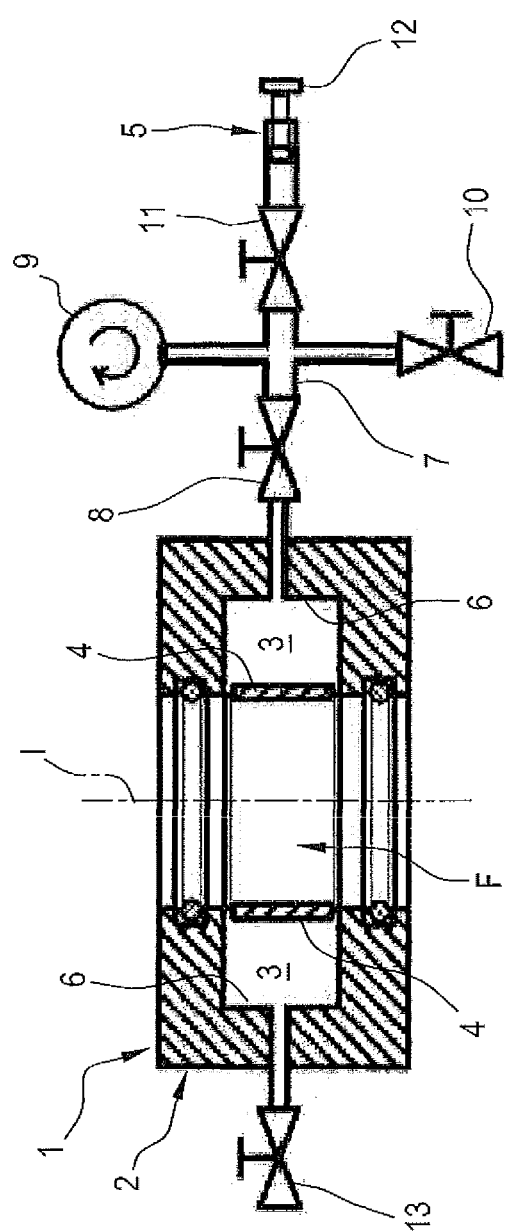
FIG. 1 shows a view, partly in cross section, of an instrument according to a possible embodiment of this description.

FIG. 1 shows a testing instrument 1 according to a possible embodiment of this description. The testing instrument 1 is configured to measure or check the degree or level of saturation of a pressure sensor unit G of a piezocone P.

In the situation of FIG. 3, the instrument 1 is fitted or mounted to the piezocone P.

In FIG. 3, the instrument 1 is shown partly in cross section in a plane containing the axis of extension X of the piezocone P, whilst the piezocone P is viewed from a plane parallel to the axis of extension X, but is not in cross section.

The instrument 1 comprises a structure 2 which extends around a passage F adapted to receive the piezocone P; the passage F is shown only in FIG. 1 and not in FIG. 3 because, in FIG. 3, it is occupied by the piezocone P, which is inserted in the passage itself.

The instrument 1 comprises a chamber 3, at least partly inside the annular structure 2, for containing a measuring liquid.

In an example embodiment of the instrument 1, the structure 2 is annular. The instrument 1 comprises a membrane 4 which delimits the chamber 3, defining an annular surface facing the passage F; the membrane 4 is adapted to be operatively in contact with the porous annular element E of the sensor unit G of the piezocone P, as shown in FIG. 3.

In an example embodiment of the instrument 1, the surface facing the passage F defined by the membrane 4 is an annular surface.

In an example embodiment of the instrument 1, the surface facing the passage F defined by the membrane 4 is a cylindrical surface.

In the embodiment of the instrument 1 shown in the accompanying drawings, the surface facing the passage F defined by the membrane 4 is an annular cylindrical surface.

The instrument 1 comprises a pressurizer 5 adapted to be in fluid communication with the chamber 3 and configured to transmit a pressure pulse of predetermined intensity to the membrane 4 through the measuring liquid contained in the chamber 3.

In an example embodiment of an instrument 1 according to this description, the structure 2 defines a concavity 6 which extends around the passage F and is directed towards the passage F. The membrane 4 is connected to the annular structure 2 and positioned to close the concavity 6 in such a way as to define the chamber 3.

In an example embodiment of an instrument 1 according to this description, the passage F around which the structure 2 extends defines an insertion axis I for inserting the piezocone P.

In FIG. 1, the instrument 1 is partly in cross section in a plane containing the insertion axis I.

In an example embodiment of the instrument 1, the surface defined by the membrane 4 and facing the passage F is parallel to the insertion axis I defined by the passage itself.

The passage is such that the axis of extension X of the piezocone P operatively coincides with the insertion axis I, as is the case shown in FIG. 3.

In an example embodiment of the instrument 1 according to this description, the membrane 4 is such that when the structure 2 is fitted to the piezocone P, as shown for example in FIG. 3, it is operatively in contact with the lateral outside surface S of the porous annular element E.

In an example embodiment of the instrument 1 according to this description, the membrane 4 is such that when the structure 2 is fitted to the piezocone P, as shown for example in FIG. 3, it faces the lateral outside surface S of the porous annular element E.

That way, the membrane 4 remains positioned around the axis of extension X of the piezocone P and the lateral outside surface S of the element E and thus around the surface portion of the piezocone P defined by the selfsame lateral outside surface S of the element E.

In FIGS. 1 and 3, the structure 2, the membrane 4 and the chamber 3 are in cross section through a plane containing the insertion axis I of the passage F or the axis of extension X of the piezocone P and thus, two parts situated on mutually opposite sides of the insertion axis I or of the axis of extension X are shown.

In an example embodiment of the instrument 1 according to this description, the chamber 3, defined by the membrane 4 and the structure 2, is an annular chamber so that the pressure pulse is distributed uniformly all around a surface portion of the piezocone P. This surface portion of the piezocone P is defined by the lateral outside surface S of the porous annular element E.

In the piezocone P of the type shown in the accompanying drawings, the surface portion is situated on the body P1 of the piezocone P.

With reference to the example piezocone P shown in the accompanying drawings, the surface defined by the membrane 4 and the chamber 3, as well as the membrane 4 itself, are both positioned, as shown in FIG. 3, around the surface portion of the body P1 of the piezocone P. In the piezocone P of the type shown in the accompanying drawings, the surface portion of the body P1 of the piezocone P is cylindrical in shape and, as stated above, coincides with the lateral outside surface S of the porous annular element E.

The pressurizer 5 may be of a type which can be activated manually. For example, it may be a screw pressurizer. The pressurizer 5 may be of any other suitable type, even with artificial feed.

In an example embodiment of the instrument 1 according to this description, the instrument 1 comprises an infeed duct 7 interposed between the pressurizer 5 and the chamber 3. The instrument 1 comprises a release valve 8 situated in the infeed duct 7 in such a way as to be able to release into the chamber 3 the pressure generated by the pressurizer 5.

The release valve 8 closes or opens the fluid communication between the infeed duct 7 and the chamber 3.

In an example embodiment of the instrument 1 according to this description, the release valve 8 is a sealed valve.

The user can operate on the pressurizer 5 to generate a pressure of desired level in the infeed duct 7 while the release valve 8 is closed. Next, the user can open the release valve 8 so that the pressure generated is propagated impulsively, and preferably at least almost instantaneously, towards the chamber 3, the membrane 4 and the sensor unit G.

The passage F is designed to allow the piezocone P to be anchored inside it and to hold it within when the pressure pulse is released.

In an example embodiment of the instrument 1 according to this description, the instrument 1 comprises an auxiliary pressure sensor positioned to measure the pressure in the infeed duct 7. In an example embodiment of the instrument 1, the instrument 1 also comprises a pressure indicator 9 connected to the auxiliary sensor to make available to the user the value of the pressure measured by the auxiliary pressure sensor.

The indicator may, for example, be analogue (for example, part of a pressure gauge) or digital. The auxiliary sensor and the indicator 9 are designed to make known the intensity or value of the pulse generated by the pressurizer 5.

In an example embodiment of the instrument 1 according to this description, the instrument 1 also comprises an infeed valve 10 to allow the measuring liquid to enter the chamber 3 through the infeed duct 7.

The instrument 1 might also comprise an intermediate valve 11 capable of closing or opening the fluid communication between the pressurizer 5 and the infeed duct 7.

The intermediate valve 11, if present, must be open to allow the pressurizer 5 to generate the pressure in the infeed duct 7.

In an example embodiment of the instrument 1 according to this description, the instrument 1 also comprises an actuator 12 with which the user can regulate the pressure generated by the pressurizer 5.

In an example embodiment of the instrument 1 according to this description, the instrument 1 also comprises a relief valve 13 in communication with the chamber 3 to remove extraneous elements from the chamber 3 and/or, if necessary, to also allow filling the chamber 3.

A possible example embodiment of a testing method for checking the degree or level of saturation of the sensor unit G comprises the following steps:
generating a pressure pulse of known intensity;
transmitting or propagating the pulse to the lateral outside surface S of the porous annular element E;
acquiring a pressure value measured by the transducer T in response to the pressure pulse transmitted;
comparing the acquired value with the known intensity of the generated pulse.

The pressure pulse may have negative or positive intensity.

In an example embodiment of the method, transmission occurs at least through a measuring liquid contained in a chamber 3. The measuring liquid, if present, preferably fills the chamber 3 completely.

In an example embodiment of the method, transmission occurs at least through a membrane 4 in contact with the lateral outside surface S of the porous annular element E and/or facing the lateral outside surface S.

In an example embodiment of the method, transmission occurs at least through a measuring liquid contained in a chamber 3 and then at least through a membrane 4 which delimits the chamber 3. Transmission occurs while the membrane 4 is in contact with the lateral outside surface S of the porous annular element E and/or faces the lateral outside surface S of the porous annular element E.

Transmission or propagation of the pulse to the lateral outside surface S of the porous annular element E causes a further transmitting step whereby the pulse is transmitted from the lateral outside surface S to the pressure transducer T, allowing the pressure value to be acquired.

It should be noted that this further transmission (inside the piezocone P) occurs at least through the porous annular element E and then at least through the duct C interposed between the porous annular element E and the pressure transducer T.

In an example embodiment of the method, this further transmission occurs at least through a working liquid contained in the sensor unit G. If the method entails transmitting the pulse through a measuring liquid contained in the chamber 3, the working liquid may be different from, or the same as, the measuring liquid.

Preferably, the working liquid completely fills the porous annular element E and/or the duct C interposed between the porous annular element E and the pressure transducer T.

The working liquid may be a liquid proper or a paste or a gel.

In an example embodiment of it, the method comprises a step of measuring the time taken by the pressure transducer T to respond to the pulse generated by the pressurizer 5.

This measuring step may be based on the difference between the instant which the acquired pressure value refers to and the instant in which the pressure pulse was generated, or it may be correlated with this difference.

In an example embodiment of it, the method comprises, before the generating step, a step of inserting the piezocone P through a passage F around which there extends an annular structure 2 inside which the chamber 3 is situated.

The inserting step is preferably carried out in such a way that the membrane 4, following insertion, is positioned around the lateral outside surface S of the porous annular element E.

The inserting step is preferably carried out in such a way that the membrane 4, following insertion, is positioned in contact with and/or facing the lateral outside surface S of the porous annular element E.

The inserting step may comprise a relative movement between the piezocone P and the instrument 1 in the direction indicated by the arrow Y in FIG. 3.

According to another aspect, this description relates to an apparatus for measuring soil interstitial pressure which develops when a piezocone P for soil stratigraphic analysis is pushed into the soil, the apparatus comprising:
a piezocone comprising a sensor unit G for measuring the interstitial pressure of the soil;
a testing instrument 1 for checking the degree of saturation of a pressure sensor unit of a piezocone P, the testing instrument 1 being according to this description.

A piezocone P which forms part of a possible example embodiment of an apparatus according to this description may comprise, for example, the features of the piezocone P shown in FIGS. 2 and 3.

A method for use of this apparatus may comprise the following steps of checking the degree of saturation of the sensor unit G:
generating a pressure pulse of known intensity;
transmitting the pulse to the lateral outside surface S of the porous annular element E;
acquiring a pressure value measured by the transducer T in response to the pressure pulse transmitted;
comparing the acquired value with the known intensity of the generated pulse.

These checking steps make up the testing method described above.

In this method for use of an apparatus according to this description, this testing method is thus applied to the sensor unit G of the piezocone P of an apparatus according to this description.

Generally speaking, a method for use of an apparatus according to this description thus comprises a testing method according to this description, having one or more of the features described above with reference to the testing method itself.

The method for use of the apparatus also comprises a step of performing at least one penetrometric test for defining the stratigraphic profile and for in situ characterization of a soil deposit using the piezocone P.

These checking steps may be carried out prior to the step of performing the penetrometric test.

These checking steps may be carried out after the step of performing the penetrometric test.

In an example embodiment of the method for use, these checking steps are carried both at least a first time prior to the step of performing the penetrometric test and at least a second time after the step of performing the penetrometric test.

That way, it is possible to check for any changes that may have occurred in the degree of saturation while the piezocone was being used for the test.

The invention claimed is:
1. A testing instrument for checking a degree of saturation of a pressure sensor unit of a piezocone, comprising:

an annular structure which extends around a passage adapted to receive the piezocone by insertion into the passage;

a chamber, at least partly inside the annular structure, for containing a measuring liquid;

a membrane which delimits the chamber, defining an annular surface facing the passage, to be operatively in contact with a porous annular element of the pressure sensor unit of the piezocone;

a pressurizer in fluid communication with the chamber and configured to transmit a pressure pulse of predetermined intensity to the membrane through the measuring liquid contained in the chamber.

2. The testing instrument according to claim 1, wherein the annular structure defines a concavity (6) which extends around the passage and is directed towards the passage, the membrane being connected to the annular structure and positioned to close the concavity in such a way as to define the chamber.

3. The testing instrument according to claim 1, wherein the passage defines an insertion axis for inserting the piezocone in such a way that an axis of extension of the piezocone operatively coincides with the insertion axis, the annular surface being preferably parallel with the insertion axis.

4. The testing instrument according to claim 1, comprising an infeed duct interposed between the pressurizer and the chamber and a release valve situated in the infeed duct in such a way as to be able to release into the chamber the pressure generated by the pressurizer.

5. The testing instrument according to claim 4, comprising an auxiliary pressure sensor positioned in such a way as to be able to measure the pressure in the infeed duct, and a pressure indicator connected to the auxiliary sensor to display the intensity of the pulse generated by the pressurizer.

6. The testing instrument according to claim 1, comprising a relief valve in communication with the chamber to remove extraneous elements from the chamber or to allow filling the chamber.

7. A testing method for checking a degree of saturation of a pressure sensor unit of a piezocone, the pressure sensor unit comprising a porous annular element whose lateral outside surface defines a surface portion of the piezocone located around an axis of extension of the piezocone, a pressure transducer inside the piezocone and a duct interposed between the porous annular element and the pressure transducer in such a way that the pressure transducer can measure a pressure applied on the surface portion, the method comprising:

generating a pressure pulse of known intensity;
transmitting the pressure pulse to the lateral outside surface of the porous annular element;
acquiring a pressure value measured by the pressure transducer in response to transmitting the pressure pulse;
comparing the acquired pressure value with the known intensity of the pressure pulse.

8. The method according to claim 7, wherein the pressure pulse is transmitted at least through a measuring liquid contained in a chamber.

9. The method according to claim 8, comprising, before generating the pressure pulse, inserting the piezocone through a passage around which there extends an annular structure inside which the chamber is situated.

10. The method according to claim 7, wherein the pressure pulse is transmitted at least through a membrane that is facing the lateral outside surface, and/or is in contact with the lateral outside surface.

11. The method according to claim 9, wherein inserting the piezocone comprises positioning the membrane around the lateral outside surface of the porous annular element.

12. The method according to claim 7, further comprising carrying out at least one penetrometric test for defining a stratigraphic profile and for in situ characterization of a soil deposit by means of the piezocone, wherein generating the pressure pulse, transmitting the pressure pulse, acquiring the pressure value, and comparing the acquired pressure value with the known intensity of the pressure pulse for checking the degree of saturation of the pressure sensor unit of the piezocone are performed before and/or after carrying out the penetrometric test.

13. An apparatus for measuring an interstitial pressure which develops when a piezocone for soil stratigraphic analysis is pushed into soil, the apparatus comprising:

a piezocone comprising a sensor unit for measuring the interstitial pressure of the soil; and
a testing instrument according to claim 1.

14. The apparatus according to claim 13, wherein the piezocone extends along an axis of extension of the piezocone, and comprises at least two strain transducers positioned to measure an axial force acting on the piezocone and a lateral friction acting on the piezocone.

15. The apparatus according to claim 13, wherein the sensor unit comprises:

a porous annular element whose lateral outside surface defines a surface portion of the piezocone situated around an axis of extension of the piezocone;
a pressure transducer inside the piezocone;
a duct interposed between the porous annular element and the transducer in such a way that the transducer can measure a pressure applied on the surface portion.

* * * * *